United States Patent [19]

Agricola et al.

[11] Patent Number: 4,902,498

[45] Date of Patent: Feb. 20, 1990

[54] ORAL COMPOSITIONS

[75] Inventors: Francis O. Agricola, Cincinnati; William E. Cooley, Wyoming, both of Ohio

[73] Assignee: The Procter & Gamble Company, Cincinnati, Ohio

[21] Appl. No.: 200,996

[22] Filed: Jun. 1, 1988

[51] Int. Cl.$^4$ .......................... A61K 7/18; A61K 7/20
[52] U.S. Cl. .......................................... 424/52; 424/53
[58] Field of Search ........................... 424/149, 52, 53

[56] References Cited

U.S. PATENT DOCUMENTS

| | | |
|---|---|---|
| 3,175,951 | 3/1965 | Tucker et al. .................. 424/52 |
| 3,494,732 | 2/1970 | Muhler ............................. 23/51 |
| 3,662,059 | 5/1972 | Wiesner et al. ................. 424/53 |
| 3,803,301 | 4/1974 | Cordon et al. ................. 424/149 |
| 3,937,806 | 2/1976 | Cooley ............................ 424/52 |
| 4,084,747 | 4/1978 | Alliger ............................. 239/4 |
| 4,330,531 | 5/1982 | Alliger ............................ 424/53 |
| 4,592,487 | 6/1986 | Simon et al. .................... 424/53 |
| 4,689,215 | 8/1987 | Ratcliff ............................ 424/53 |
| 4,690,772 | 9/1987 | Tell et al. ....................... 424/149 |

FOREIGN PATENT DOCUMENTS 2329753 12/1973 Fed. Rep. of Germany .
1288892  9/1972 United Kingdom .

*Primary Examiner*—Shep K. Rose
*Attorney, Agent, or Firm*—Richard C. Witte; Jack D. Schaeffer; Douglas C. Mohl

[57] ABSTRACT

Oral compositions, such as toothpastes, mouthwashes, lozenges and chewing gum, containing a chlorous acid liberating material, and an antidemineralization agent such as indium are disclosed.

8 Claims, No Drawings

ORAL COMPOSITIONS

TECHNICAL FIELD

The present invention relates to oral compositions containing a chlorous acid liberating material and an antidemineralization agent which compositions are effective against plaque and gingivitis and inhibit demineralization of dental enamel.

BACKGROUND ART

The use of antimicrobial agents to reduce plaque/gingivitis as well as mouth odor has been recognized for many years. Included among references disclosing oral compositions containing antimicrobials are U.S. Pat. No. 3,937,805, Feb. 10, 1976 to Harrison; U.S. Pat. No. 3,937,807, Feb. 10, 1976 to Haefele; U.S. Pat. No. 4,080,441, Mar. 21, 1978 to Gaffar et al.; U.S. Pat. No. 4,118,474, Oct. 3, 1978 to Gaffar et al.; U.S. Pat. No. 4,241,049, Dec. 23, 1980 to Colodney et al.; U.S. Pat. No. 3.925,543, Dec. 9, 1975 to Donohue; and U.S. Pat. No. 4,256,731, Mar. 17, 1981 to Curtis et al.

In addition to the materials mentioned in the patent set forth above, the prior art discloses the use of chlorine dioxide ($ClO_2$) or chlorous acid ($HClO_2$) liberating materials in oral products. One such reference is German Application 2329753, Dec. 13, 1973, to National Patent Development Corporation. The compositions in this reference are primarily alkaline but they may be acidic.

The German reference and other prior art disclosures which disclose chlorine dioxide or chlorous acid liberating materials in oral products do not recognize the problems associated with such systems when they are formulated at acidic pH's to maximize their effectiveness. Low pH's (i.e., below about 5.5) can possibly cause demineralization of dental enamel.

A way recognized in the prior art to reduce demineralization of dental enamel is through the use of indium (III) ions. A reference disclosing such systems is U.S. Pat. No. 3,175,951, Mar. 30, 1965, to Tucker, incorporated herein by reference. The present inventors have surprisingly found that the use of an antidemineralization agent in combination with a chlorine dioxide or chlorous acid liberating agent does not interfere with the effectiveness of the liberating agent while still providing antidemineralization properties.

It is an object therefore to provide oral products which are effective against plaque and gingivitis.

It is a further object of the present invention to provide oral products which are effective against plaque and gingivitis while not being injurious to hard tissue surfaces in the oral cavity.

It is still a further object of the present invention to provide products utilizing a chlorous acid liberating agent as the active.

It is still a further object of the present invention to provide an effective method of treating plaque and gingivitis.

These and additional objectives will become readily apparent from the detailed description which follows. All percentages and ratios herein are by weight unless otherwise specified. Additionally, all measurements are made at 25° C. unless otherwise specified.

SUMMARY OF THE INVENTION

The present invention relates to oral compositions which provide antiplaque and antigingivitis benefits while also not being damaging to hard tissue comprising:

(a) a safe and effective amount of a chlorous acid liberating compound;
(b) an amount of protic acid sufficient to lower and buffer the pH of the composition to less than about 5.5;
(c) an antidemineralization agent; and
(d) a pharmaceutically acceptable carrier.

These and other components will be described in detail hereinafter.

By "safe and effective amount", as used herein, means sufficient compound to reduce plaque/gingivitis and mouth odor while being safe to the hard and soft tissues or the oral cavity.

By the term "comprising", as used herein, is meant that various additional components can be conjointly employed in the compositions of this invention as long as the active ingredients can perform their intended functions.

By the term "pharmaceutically acceptable carrier", as used herein, is meant a suitable vehicle which can be used to apply the present compositions in the oral cavity.

Chlorous Acid Liberating Compound

The present invention employs a chlorous acid liberating compound as one of the components of the composition claimed herein. By "chlorous acid liberating compound" is meant any compound which when appropriately treated will liberate chlorous acid. While any chlorous acid liberating compound may be used, water-soluble chlorites are preferred because they are readily available and inexpensive. Typical water-soluble chlorites include alkali metal chlorites and alkaline earth metal chlorites. Sodium chlorite and potassium chlorite are preferred. Sodium chlorite is particularly preferred.

The amount of chlorous acid liberating compound that is used in the present compositions may be generally from about 0.01 to about 10, typically from about 0.10 to about 3.0, and preferably from about 0.20 to about 1.0% by weight of the total composition.

Protic Acid

The protic acid used in the present invention may be any protic acid such as α-hydroxy carboxylic acids and amino acids among others. Exemplary acids include citric, malic, tartaric, glycolic, mandelic, salicylic, aspartic, carbonic, phosphoric or other structurally similar acids. Materials such a glycine or glycine hydrochloride may also be used. Mixtures of two or more such protic acids may also be used.

The pK of of these organic acids may be generally from about 2.0 to about 5.0, and preferably from about 2.5 to about 4.0.

The amount of protic acid used should be sufficient to lower the pH of the composition to less than about 5.5, typically from about 2 to about 5, and preferably from about 2.5 to about 3.0. Furthermore, this amount may be generally from about 0.01 to about 6, typically from about 0.05 to about 3, and preferably from about 0.1 to about 2% by weight of the total composition.

The chlorous acid liberating compound is generally kept separate from the protic acid prior to use in order to avoid premature reaction of the ingredients.

Antidemineralization Agent

The antidemineralization agent used in the present compositions can be any of water soluble salts of stannous, indium (III) or calcium or an inorganic phosphate salt. The amount of the indium (III) or stannous salt should be sufficient to provide from about 1 to about 1000 ppm indium (III) or stannous while the amount of the calcium salt should be sufficient to provide the same amount of calcium ions. The amount of the inorganic phosphate salt should be sufficient to provide from about 1 to about 50,000 ppm phosphate ion. The phosphate salt is preferably used in combination with calcium salts and in amounts which avoid precipitation of insoluble salts.

The indium, stannous and calcium salts can be any salts which provide the necessary levels of ions. Suitable counter ions include chloride, bromide, and fluoride for indium and stannous and chloride and bromide for calcium as well as organic acid salts of calcium.

The phosphate salt can also be any phosphate salt which provide the necessary levels of ions. Suitable counter-ions include alkali metal salts. Preferred are sodium and potassium.

The action of these agents is enhanced when used in combination with fluoride ions. It is preferred to provide a weight ratio of In (III) to $F^-$ within the range of about 1:1 to about 1:500, preferably about 1:5. The weight ratio of $Ca^{2+}$ to $F^-$ is within the range of from about 1:1 to about 1:100.

Pharmaceutically Acceptable Carrier

The carrier(s) for chlorous acid liberating compound and the protic acid compound can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

Dentifrices preferably contain from about 0.05% to 10% by weight of the chlorous acid liberating component. Dentifrices also contain an abrasive polishing material and typically also contain sudsing agents, flavoring agents and sweetening agents. Toothpaste compositions additionally contain binders, humectants and water.

The dentifrice abrasive, generally has a particle size of from about 0.1 to about 10 microns in diameter and can be any abrasive polishing material which does not excessively abrade tooth dentin. These include, for example, silica, both precipitated and gels, calcium carbonate, dicalcium orthophosphate dihydrate, calcium pyrophosphate, calcium polymetaphosphate and insoluble sodium polymetaphosphate. Preferably, however, the abrasive is one which has a high degree of compatibility at low pH's with the chlorous acid liberating compounds and fluoride ions. These include, for example silica xerogels such as those described in U.S. Pat. No. 3,538,230 to Pader et al., issued Nov. 3, 1970; hydrofluoric acid-treated amorphous silica abrasives such as those disclosed in U.S. Pat. No. 3,862,307 to DiGiulio, issued Jan. 21, 1975; mineral abrasives coated with cationic polymers such as those disclosed by J. J. Benedict in U.S. Pat. No. 4,157,387, issued June 5, 1979; and condensation products of urea and formaldehyde such as those disclosed in Cooley et al., in U.S. Pat. No. 3,070,510, issued Dec. 24, 1972. All of these patents are incorporated herein by reference.

The total amount of abrasive materials in the dentifrice embodiments of this invention can range from about 0.5% to about 95% by weight of the dentifrice. Preferably toothpastes contain from about 6% to about 60% by weight and toothpowders contain from about 20% to about 95% by weight abrasives.

Dentifrice compositions can also contain emulsifying agents. Suitable emulsifying agents are those which are reasonably stable and foam throughout a wide pH range, including non-soap nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide anticaries effectiveness. The fluoride compounds are believed to provide protection against demineralization as well as aid in remineralization of dental enamel. Preferred fluorides are sodium fluoride, stannous fluoride, indium fluoride, and sodium monofluorophosphate. Norris et al., U.S. Pat. No. 2,946,725, issued July 26, 1960 and Widder et al., U.S. Pat. No. 3,678,154, issued July 18, 1972 disclose such salts as well as others.

In preparing toothpastes, it is necessary to add some thickening material to provide a desirable consistency. Preferred thickening agents are carboxyvinyl polymers, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols.

The humectant can comprise up to about 65% by weight of the toothpaste composition.

With both humectants and binders, care must be taken if these are combined with the chlorous acid liberating compound that they do not activate the compound before the product is used.

Flavoring agents can also be added to dentifrice compositions. Suitable flavoring agents include oil of wintergreen, oil of peppermint, menthol, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Another preferred embodiment of the present invention is a mouthwash composition. Conventional mouthwash composition components can comprise the carrier for the chlorous acid liberating component of the present invention. Mouthwashes generally comprise about 20:1 to about 2:1 of a water/ethyl alcohol solution and preferably other ingredients such as fluoride ion sources, flavor, sweeteners, humectants, and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to about 1.67% fluoride ions (preferably from about 0.0017% to about 0.67%), 0% to 0.3% (preferably 0.03% to 0.3%) flavoring agent, and the balance water. The amount of chlorous acid liberating compound in mouthwashes is typically from about 0.01 to about 0.5% by weight.

Suitable lozenge and chewing gum components are disclosed in U.S. Pat. No. 4,083,955, Apr. 11, 1978 to Grabenstetter et al., incorporated herein by reference.

METHOD OF MANUFACTURE

The carrier compositions of the present invention can be made using methods which are common in the oral products area.

COMPOSITION USE

The present invention in its method aspect involves applying to the oral cavity safe and effective amounts of the compositions. Generally an amount of the composition to provide at least about 50 ppm of chlorous acid is effective.

The following examples further describe and demonstrate preferred embodiments within the scope of the present invention. The examples are given solely for illustration and are not to be construed as limitations of this invention as many variations thereof are possible without departing from the spirit and scope thereof. All of the examples are of rinses since rinses are the preferred vehicle.

EXAMPLE I

| ACTIVATOR | | BASE | |
|---|---|---|---|
| Component | Wt. % | Component | Wt. % |
| Malic acid | 0.75 | $NaClO_2$ | 0.30 |
| Glycerin | 20.0 | NaF | 0.10 |
| Ethanol | 16.0 | Water | q.s. |
| Menthol | 0.03 | | |
| Na saccharin | 0.05 | | |
| $InCl_3$ | 0.02 | | |
| FD&C Blue #1 | 0.02 | | |
| Water | q.s. | | |

After mixing in 1:1 vol:vol ratio, final pH=3±0.2, final $F^-$=225 ppm, and final In(III)=50 ppm.

EXAMPLE II

| ACTIVATOR | | BASE | |
|---|---|---|---|
| Component | Wt. % | Component | Wt. % |
| Citric acid | 0.30 | $NaClO_2$ | 0.30 |
| $Na_3$ citrate | 0.42 | NaF | 0.10 |
| Glycerin | 20.0 | Water | q.s. |
| Ethanol | 16.00 | | |
| Menthol | 0.025 | | |
| Na saccharin | 0.025 | | |
| D-ribose | 2.00 | | |
| $NaH_2PO_4$ | 2.00 | | |
| $CaCl_2\cdot 2H_2O$ | 0.03 | | |
| FD&C Blue #1 | 0.02 | | |
| Water | q.s. | | |

After mixing in 1:1 vol:vol ratio, final pH=4.5±0.2, final $F^-$=225 ppm, and final $Ca^{+2}$=40 ppm.

EXAMPLE III

| ACTIVATOR | | BASE | |
|---|---|---|---|
| Component | Wt. % | Component | Wt. % |
| Glycine | 1.0 | $NaClO_2$ | 0.30 |
| Sorbitol | 20.00 | NaF | 0.10 |
| Na benzoate | 0.05 | Water | q.s. |
| Methyl salicylate | 0.10 | | |
| Na saccharin | 0.10 | | |
| $InCl_3$ | 0.02 | | |
| FD&C Blue #1 | 0.03 | | |
| FD&C Yellow #5 | 0.03 | | |
| HCl to adjust pH to 3 | | | |
| Water | q.s. | | |

After mixing in 1:1 vol:vol ratio, final pH=3.2±0.2, final $F^-$=225 ppm, and final In(III)=50 ppm.

EXAMPLE IV

| ACTIVATOR | | BASE | |
|---|---|---|---|
| Component | Wt. % | Component | Wt. % |
| Aspartic acid | 0.5 | $NaClO_2$ | 0.45 |
| Sorbitol | 20.0 | Water | q.s. |
| Ethanol | 16.0 | | |
| Xylitol | 8.0 | | |
| Peppermint Oil | 0.2 | | |
| $InCl_3$ | 0.01 | | |
| $NaH_2PO_4$ | 1.0 | | |
| FD&C Blue #1 | 0.05 | | |
| Adjust pH to 3.5 | | | |
| Water | q.s. | | |

After mixing in 1:1 vol:vol ratio, final pH=3.5+0.2, final In(III)=25 ppm.

Indium salts and calcium salts are preferably added when rinse is at lowest pH to aid in dissolution.

In addition to $NaClO_2$, other alkali metal salts such as $KClO_2$ or $LiClO_2$ or alkaline earth salts such as $Ca(ClO)_2$ may be used with similar results being obtained. Acids other than those indicated such as tartaric acid, mandelic acid, salicylic acid and carbonic acids may also be used. Mixtures of acids may also be used.

What is claimed is:

1. In an oral composition containing fluoride and a water-soluble chlorite chlorous acid liberating antiplaque antigingivitis component, a safe and effective improvement, effective to obtain fluoride ion enhanced anti-demineralization without causing demineralization of dental enamel below pH of about 5.5, wherein a base containing the soluble fluoride ion salt and water soluble chlorite is kept separate, prior to mixing, from an activator containing at least one acid selected from the group consisting of citric, malic, tartaric, glycolic, mandelic, aspartic, salicylic, phosphoric and carbonic acids and glycine in an amount sufficient to lower the pH of the composition from about 2 to about 5 and a water soluble indium salt anti-demineralization agent.

2. The composition of claim 1 wherein said composition contains from about 0.01 to about 10 percent by weight metal chlorite based upon the total weight of said composition.

3. The composition of claim 1 wherein said composition contains from about 0.10 to about 3.0 percent by weight metal chlorite based upon the total weight of said composition.

4. The composition of claim 1 wherein said composition contains up to about 0.3 percent by weight metal chlorite based upon the total weight of said composition.

5. The composition of claim 1 wherein said composition contains from about 0.10 percent to about 3.0 percent by weight metal chlorite based upon the total weight of said composition.

6. The composition of claim 1 wherein said composition contains from about 0.2 percent to about 1 percent by weight metal chlorite based upon the total weight of said composition.

7. The composition of claim 1 wherein the weight ratio of I (III) to $F^-$ is from about 1:1 to about 1:500.

8. A method of reducing plaque/gingivitis by applying to the oral cavity a safe and effective amount of a composition according to claim 1.

* * * * *